United States Patent [19]

Chow et al.

[11] 4,283,551

[45] Aug. 11, 1981

[54] NOVEL ACETYLENE END-CAPPED POLYESTERS

[75] Inventors: Wai Y. Chow; Daniel J. Hurley; James H. Rea; S. Paul Thackaberry, all of Houston, Tex.

[73] Assignee: Gulf Oil Corporation, Pittsburgh, Pa.

[21] Appl. No.: 75,364

[22] Filed: Sep. 13, 1979

[51] Int. Cl.$^3$ .............................................. C07C 69/76
[52] U.S. Cl. ...................................... 560/86; 560/11; 560/18; 560/52; 560/73; 560/83
[58] Field of Search ....................... 560/18, 52, 72, 80, 560/83, 86, 95; 526/285

[56] References Cited

U.S. PATENT DOCUMENTS

| | | | |
|---|---|---|---|
| 2,979,538 | 4/1961 | Wotiz | 560/95 |
| 3,306,928 | 2/1967 | Lux et al. | 560/95 |
| 3,872,154 | 3/1975 | Hirzy | 560/95 |
| 3,996,380 | 12/1976 | Henrick | 560/95 |
| 4,168,360 | 9/1979 | D'Alelio | 525/426 |
| 4,168,366 | 9/1979 | D'Alelio | 525/426 |

FOREIGN PATENT DOCUMENTS 420612  3/1972  U.S.S.R. ................... 560/95

*Primary Examiner*—Lucille M. Phynes
*Attorney, Agent, or Firm*—Richard L. Kelly

[57] ABSTRACT

A group of heat curable resins are provided which have good physical properties, which properties are retained to a surprising degree after prolonged exposure to temperatures as high as 300° C. The products are acetylene end-capped polyesters prepared by reacting a hydroxyphenylacetylene with a diacid chloride of an aromatic dibasic acid such as 4,4'-benzophenone dicarboxylic acid dichloride.

4 Claims, No Drawings

NOVEL ACETYLENE END-CAPPED POLYESTERS

BACKGROUND OF THE INVENTION

There is a growing interest in the art in the development of polymeric materials which have good strength and retain a considerable portion of their strength after extended exposure to high temperature. Acetylene end-capped polyimide oligomers of the type disclosed in U.S. Pat. No. 3,845,018 and U.S. Pat. No. 3,897,349 are a prime example of products having this combination of properties.

Polyimides of the type referred to above, while having excellent physical properties and good retention of these physical properties after prolonged exposure to high temperature, are subject to two recognized shortcomings. First, these polyimides must be prepared from aromatic diamines of specific structures to obtain the desired high temperature performance properties. Unfortunately, such aromatic diamines are difficult to synthesize and are expensive. In addition, the melting points of the polyimides are very close to their curing temperatures. For this reason, the polyimides are difficult to process. In particular, they are very difficult to mold.

For the above reasons, there is a continuing need in the art for heat-curable resins having good high temperature performance properties and which can be prepared at more moderate cost. In addition, there is a need in the art for resins of this type which can be more readily processed and, in particular, can be more readily molded.

SUMMARY OF THE INVENTION

The products of the invention are heat-curable polyesters having the structure:

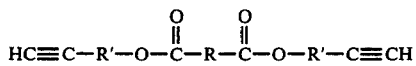
(1)

where R is a phenylene group, a naphthylene group, or the structure:

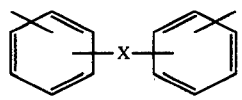

where X is

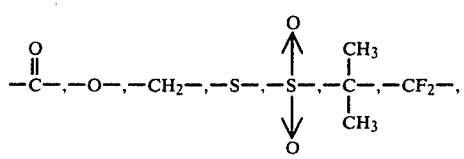

or a bond, or the structure:

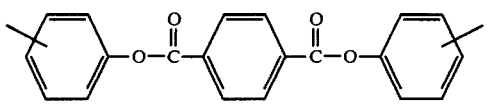

and R' is a phenylene group.

The products of the invention cure rapidly to form infusible thermoset products when heated to about 270° C. The products have good mechanical properties which are retained to a surprising degree even when heated for extended periods at temperatures as high as 316° C. (600° F.).

DETAILED DESCRIPTION OF THE INVENTION

The acetylene end-capped polyesters of the invention are prepared by reacting a hydroxyphenylacetylene with a diacid chloride of an aromatic dibasic acid having an acid group on each end of the molecule.

The hydroxyphenylacetylenes employed in preparing the products of the invention have the structure:

$$HO—R'—C\equiv CH \quad (2)$$

where R' is a phenylene group. Examples of suitable hydroxyphenylacetylenes include 3-hydroxyphenylacetylene, 4-hydroxyphenylacetylene and analogues thereof containing halogen atoms and/or alkyl groups attached to the phenyl ring. The hydroxyphenylacetylenes can be prepared by diazotization of the corresponding aminophenylacetylene or by the method disclosed by Bohlmann, Albrecht and Schmidt, *Chem. Ber.*, 99, 2822 (1966).

The diacid chlorides of aromatic dibasic acids employed in preparing the products of the invention have the structure:

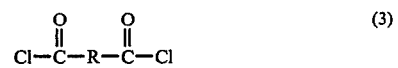
(3)

where R has the same significance as in formula (1).

The reaction is conducted between 1 mol of the diacid chloride of formula (3) and 2 mols of the hydroxyphenylacetylene. The reaction preferably is carried out in a solvent having good solvent power for both reactants. Polychlorinated hydrocarbons, such as 1,1,2,2-tetrachloroethane (TCE), are the presently-preferred solvents. Since hydrogen chloride is formed as a coproduct, an acid acceptor, such as an amine, preferably is included in the reaction mixture. The amine is employed in a quantity at least molarly equivalent to the hydroxyphenylacetylene. The reaction preferably is run at low temperatures, e.g., below 10° C., with one of the reactants being added to the other with stirring.

Utility of Products

The acetylene end-capped polyesters of the invention can be molded and heat cured to provide moldings having excellent strength, which strength is retained to a surprising degree even after the molded articles are heated for extended periods of time at elevated temperatures, e.g., 500 or more hours at 315° C. (600° F.). Moreover, the products before being cured have adequate flow to be processed satisfactorily. Because of their relatively low melting points and long gel times, these products are particularly well suited for fabrication by injection molding.

In addition to being employed to prepare moldings, the acetylene end-capped polyesters can be used to lay down tough coatings on substrates such as metals and to prepare laminates and/or composite structures. To prepare such structures, a web of inorganic fibers such as glass, quartz, graphite fibers or the like, is impregnated with a solution containing the polyester solids. The impregnated web then is heated to cross-link the polyester.

The coating and laminating varnishes can be prepared by dissolving the polyester in a suitable solvent. Dimethyl acetamide (DMA), dimethyl formamide (DMF) and N-methyl-2-pyrrolidone (NMP) are suitable solvents.

When used as coating compositions, the polyester solution should be laid down on the substrate and heat cured at temperatures of 270° C. or higher. Somewhat lower curing temperatures can be employed if longer curing times are employed. The optimization of curing times and temperatures can be established readily through routine experimentation within the skill of the art.

To prepare laminates, the desired web should be impregnated with the polyester solution and heated to an elevated temperature for a time sufficient to evaporate the solvent therefrom. Drying the impregnated web for 60 minutes at 150° C. or 80 minutes at 135° C. in a circulating air oven is usually sufficient. The dried webs then can be laid up and heated under pressure to cross-link the resin solids. Modest pressures of the order of 15–200 psig are sufficient. Curing temperatures of the order of 250°–400° C. and preferably 275°–325° C. are employed for curing times of the order of 1–12 hours. Optimum properties are developed by post curing the laminates for periods of 16–48 hours at temperatures of about 260°–375° C.

Laminates having excellent physical properties can be prepared from the polyesters of the invention by the following procedures. Impregnate graphite tapes, e.g., 5" wide tapes of a commercial product sold under the name Celion 3000, having an O twist, and bearing an NR 150-B2 surface size. The polyester solution employed should have a high solids content, preferably at least 25 weight %. The tapes should be impregnated and dried until they contain about 40 weight % resin solids. Typically the prepregs will be 2.5 mils thick. A laminate lay-up then is made from 32 plys with the prepregs all being aligned in one direction. The lay-up is laminated by a vacuum bag technique with the assembly being heated from ambient temperature to 265° F. with the temperature being increased at a rate of about 5°/minute under a vacuum of 15 inches of Hg. The assembly is maintained for an additional 2-hour period under 15 inches of Hg. The pressure then is reduced to the maximum vacuum that can be drawn and the temperature is increased to 525° F. at a rate of about 7° F./minute. The laminate is held at 525° F. for an additional period of 2 hours. The laminate is cooled to room temperature over a period of 5 hours. The laminate is post cured by heating from room temperature to 650° F. at a rate of 5°–10° F./minute and then heating for 13 hours at 650° F. The temperature then is increased to 700° F. at a rate of 5°–10° F./minute. The temperature then is held at 700° F. for an additional 4 hours.

The physical properties of moldings, coatings and composites prepared from the polyesters of the invention closely approximate those prepared from the polyimide oligomers disclosed in U.S. Pat. No. 3,897,349 and U.S. Pat. No. 3,845,018.

The following examples are set forth to illustrate the principle and practice of the invention to those skilled in the art. Where parts and percentages are set forth, unless otherwise noted, they are parts and percentages set forth on a weight basis.

EXAMPLE 1

A flask equipped with a stirrer was charged with 1.18 gm (0.01 mol) of 3-hydroxyphenylacetylene, 1 gm (0.01 mol) of triethylamine, and 50 ml of 1,1,2,2-tetrachloroethane (TCE). The flask was cooled to below 10° C. with an ice bath and 1.5 gm (0.005 mol) of 4,4-benzophenone dicarboxylic acid dichloride was added to the flask with stirring over a period of about 10 minutes. The originally charged solution had a purple color which turned brown upon the addition of the acid chloride. The flask was stirred for 120 minutes at the ice temperature and then was allowed to warm to room temperature over a period of two hours. The reaction solution was yellow in color and slightly cloudy, presumably by reason of the presence of the triethylamine hydrochloride salt. The reaction mixture was filtered and the filtrate was added to 150 ml of ethanol to precipitate the desired product. After drying, the product melted at 183°–186° C. The infrared and nuclear magnetic resonance spectra of the product were consistent with the proposed structure. The product had a gel time of 1147 seconds at 218° C. and a gel time of 150 seconds at 245° C.

EXAMPLE 2

Example 1 was repeated except that terphthaloyl dichloride was substituted for the 4,4'-benzophenone dicarboxylic acid dichloride. The product melted at 167°–176° C. The infrared and nuclear magnetic resonance spectra were consistent with the proposed structure. The product had a gel time of 145 seconds at 220° C. and a gel time of 46 seconds at 250 ° C.

EXAMPLE 3

Part A

A three-necked round bottom flask, equipped with a mechanical stirrer, a dropping funnel, and a condenser, was charged with 27.6 gm (0.2 mol) of p-hydroxybenzoic acid, 15.8 gm (0.2 mol) pyridine and 250 ml of tetrahydrofuran (THF). The system was flushed with nitrogen by means of a gas inlet attached to the top of the condenser. The solution was cooled to below 10° C. with an ice bath and 20.3 gm (0.1 mol) of terephthaloyl dichloride dissolved in 150 ml of THF was added to the flask, dropwise, over a period of 1.5 hours. The mixture was stirred for an additional 1.5 hours and filtered. The solvent was removed by evaporation and the product was dried in a vacuum oven for 16 hours at 100° C. to obtain a 92% yield. The infra red spectrum was consistent with that of a polyester obtained by reacting the hydroxy group of the hydroxybenzoic acid with the acid chloride groups.

Part B

A round bottom flask equipped with a condenser was charged with 30 gms of the product of Part A, 200 ml of thionyl chloride and 5 drops of dimethylformamide. The reaction mixture was refluxed for three hours to convert the carboxylic groups of the product of Part A to the corresponding acid chloride groups. The excess thionyl chloride then was removed by evaporation. The solid product then was dissolved by charging to the flask TCE and heating the mixture with stirring. The reaction mixture was filtered, approximately one-half of the TCE was evaporated, and the product was precipitated from the concentrated filtrate by the addition of a large volume of hexane. After filtration, the white product was dried at 50° C. for 16 hours in a vacuum oven. The infrared spectrum was consistent with the proposed structure for the diacid chloride of the product obtained in Part A.

Part C

A three-neck round bottom flask, equipped with a mechanical stirrer, dropping funnel, and a condenser, was charged with 2.4 gm (0.02 mol) of 3-hydroxyphenylacetylene and 20 ml of TCE. The system was flushed with nitrogen by means of a gas inlet attached to the top of the condenser. The solution was cooled to below 10° C. with an ice bath and 4.4 gm (0.01 mol) of the product of Part B, and 2 gm (0.02 mol) of triethylamine dissolved in 200 ml of TCE were added, dropwise, over a period of 30 minutes. The reaction mixture was stirred for another 45 minutes, was filtered, and the desired product was precipitated from the filtrate by adding thereto about 70 ml of absolute alcohol. After filtration and drying in a vacuum oven at 70° C. for 16 hours, the desired product was obtained in a 67% yield. The infrared and nuclear magnetic resonance spectra were consistent with the proposed structure. The product melted at 135° C. and had a gel time of 1 hour at 150° C.

What is claimed:

1. A heat-curable acetylene end-capped polyester having the structure:

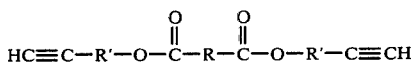

where R is a phenylene group, a naphthylene group, or the structure:

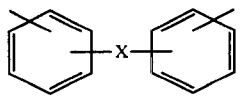

where X is

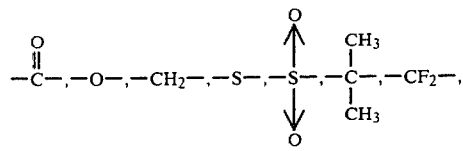

or a bond, or the structure:

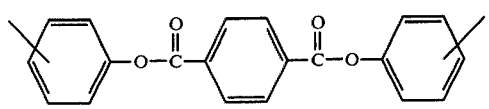

and R' is a phenylene group.

2. A product of claim 1 in which R has the structure:

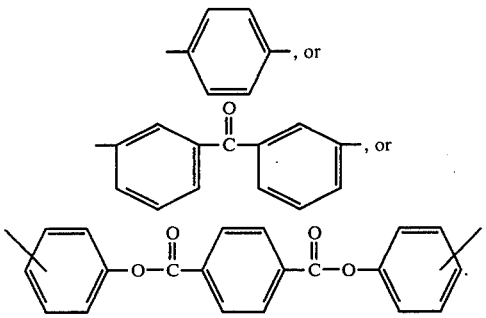

3. A method for preparing a product of claim 1 which consists essentially of reacting 2 molar portions of a hydroxyphenylacetylene with 1 molar portion of a diacid chloride in a solvent having good solvent power for both reactants at a temperature below 10° C. and in the presence of an acid acceptor which reacts with the hydrogen chloride formed as a coproduct; said diacid chloride having the structure:

where R is a phenylene group, a naphthylene group, or the structure:

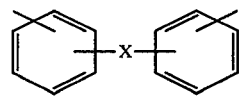

where X is

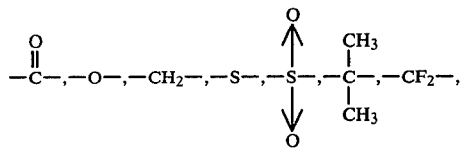

or a bond, or the structure:

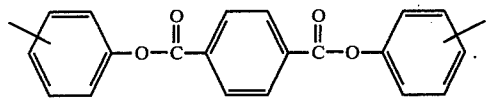

4. The method of claim 3 in which R has the structure:

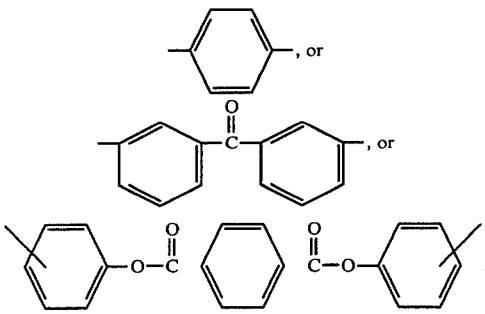

* * * * *